(12) United States Patent
Mataga et al.

(10) Patent No.: US 8,921,791 B2
(45) Date of Patent: Dec. 30, 2014

(54) INFRARED RAY SENSOR, INFRARED RAY DETECTION DEVICE, AND ELECTRONIC APPARATUS

(75) Inventors: Junichiro Mataga, Tokyo (JP); Mizuki Iwanami, Tokyo (JP); Hiroshi Sakai, Tokyo (JP); Masatake Takahashi, Tokyo (JP); Yasuhiro Sasaki, Tokyo (JP)

(73) Assignee: NEC Corporation, Tokyo (JP)

( * ) Notice: Subject to any disclaimer, the term of this patent is extended or adjusted under 35 U.S.C. 154(b) by 252 days.

(21) Appl. No.: 13/521,353

(22) PCT Filed: Nov. 19, 2010

(86) PCT No.: PCT/JP2010/006796
§ 371 (c)(1),
(2), (4) Date: Jul. 10, 2012

(87) PCT Pub. No.: WO2011/101938
PCT Pub. Date: Aug. 25, 2011

(65) Prior Publication Data
US 2012/0312988 A1   Dec. 13, 2012

(30) Foreign Application Priority Data

Feb. 16, 2010   (JP) ................................. 2010-031534

(51) Int. Cl.
| | |
|---|---|
| *G01J 5/00* | (2006.01) |
| *G01J 5/10* | (2006.01) |
| *H01L 37/02* | (2006.01) |
| *G01N 21/35* | (2014.01) |
| *G01J 5/06* | (2006.01) |

(52) U.S. Cl.
CPC . *G01J 5/10* (2013.01); *H01L 37/02* (2013.01); *G01N 21/3504* (2013.01); *G01J 2005/068* (2013.01); *G01N 21/35* (2013.01)
USPC ....................................... 250/338.3; 374/121

(58) Field of Classification Search
CPC .... G01J 5/48; G01N 21/35; H01C 7/02–7/22; H01L 27/14; H01L 31/00–31/02; H01L 31/08; H04N 5/30–5/335

USPC .......................................... 250/338.3, DIG. 1
See application file for complete search history.

(56) References Cited

U.S. PATENT DOCUMENTS

| | | | |
|---|---|---|---|
| 2009/0001553 A1* | 1/2009 | Pahl et al. ..................... | 257/704 |
| 2009/0072143 A1 | 3/2009 | Ishida et al. | |
| 2009/0184244 A1* | 7/2009 | Drews et al. .................. | 250/330 |

FOREIGN PATENT DOCUMENTS

| | | |
|---|---|---|
| CN | 85103349 A | 11/1986 |
| JP | 48-96098 A | 12/1973 |

(Continued)

OTHER PUBLICATIONS

International Search Report for PCT/JP2010/006796 dated Feb. 22, 2011.

(Continued)

*Primary Examiner* — Kiho Kim
(74) *Attorney, Agent, or Firm* — Sughrue Mion, PLLC

(57) ABSTRACT

Provided is an infrared ray sensor that can conduct a plurality of different types of detection such as temperature detection and gas detection in a simple structure and that is small size and low cost. The infrared ray sensor (1) includes, on one base (10), a first infrared ray detection unit (31) including at least one infrared ray detection element (20) including an infrared ray detection material (22) with physical properties changing depending on properties of incident infrared rays and receives and detects ambient infrared rays, and a second infrared ray detection unit (32) including at least one infrared ray detection element (20) having an identical element structure to the infrared ray detection element of the first infrared ray detection unit (31), is irradiated with infrared rays X for measurement having specific physical properties, and detects a change in the physical properties of the infrared rays X for measurement.

10 Claims, 5 Drawing Sheets

(56) References Cited

FOREIGN PATENT DOCUMENTS

| | | |
|---|---|---|
| JP | 3-134798 A | 6/1991 |
| JP | 3-82487 U | 8/1991 |
| JP | 4-158583 A | 6/1992 |
| JP | 5-60604 A | 3/1993 |
| JP | 5-346346 A | 12/1993 |
| JP | 7-92025 A | 4/1995 |
| JP | 8-271418 A | 10/1996 |
| JP | 11-167687 A | 6/1999 |
| JP | 2949286 B2 | 9/1999 |
| JP | 2007-292461 A | 11/2007 |
| WO | 2007/108441 A1 | 9/2007 |

OTHER PUBLICATIONS

Chinese Office Action issued Mar. 17, 2014 in corresponding Chinese Patent Application No. 201080064016.9.

* cited by examiner

INFRARED RAY SENSOR, INFRARED RAY DETECTION DEVICE, AND ELECTRONIC APPARATUS

CROSS REFERENCE TO RELATED APPLICATIONS

This application is a National Stage of International Application No. PCT/JP2010/006796 filed Nov. 19, 2010, claiming priority based on Japanese Patent Application No. 2010-031534 filed Feb. 16, 2010, the contents of all of which are incorporated herein by reference in their entirety.

TECHNICAL FIELD

The present invention relates to an infrared ray sensor, an infrared ray detection device using the same, and an electronic apparatus including the infrared ray detection device and an electronic component.

BACKGROUND ART

A pyroelectric infrared ray sensor using the pyroelectric effect, a variable resistance infrared ray sensor using the rate of change with temperature of the resistance of a material, a junction type infrared ray sensor using a change in electrical properties of a semiconductor p-n junction and the like are known as infrared ray sensors. The pyroelectric and variable resistance infrared ray sensors that can operate at room temperature are used for fire detection, human body detection and the like. In such an infrared ray sensor, a plurality of infrared ray detection elements are arranged in an array, so that a highly sensitive sensor can be obtained.

An infrared ray sensor that includes a linear array type pyroelectric element (10) in which a plurality of receiving surface electrodes (2a, 2b etc.) in a line pattern are formed on the front surface of a pyroelectric base (1), and a plurality of counter surface electrodes (4a, 4b etc.) in the same pattern are formed on the rear surface thereof and further includes thereon an infrared ray pass filter (50) that allows only infrared rays with a desired wavelength to pass and a lens dome (60) including a spherical Fresnel lens is illustrated in FIGS. 1 and 2 of Patent Literature 1 (FIG. 4). In this structure, infrared rays generated in a detection area are condensed by the Fresnel lens (60) and incident on the pyroelectric element (10), so that infrared rays over a wide range can be detected.

A linear array type infrared ray sensor in which a plurality of pyroelectric elements (11) in a line pattern having electrodes formed on both surfaces of pyroelectric ceramics are mounted on an element support (14) is illustrated in FIG. 1 of Patent Literature 2.

In order to detect infrared rays over a wide range without using a condenser lens such as a Fresnel lens in the pyroelectric infrared ray sensor, a pyroelectric base (2) that has been patterned into a shape capable of condensing light is proposed in FIG. 1 of Patent Literature 3, for example.

A $CO_2$ concentration detector including a light emitting unit that emits infrared rays in a wavelength band for absorbing carbon dioxide and a pyroelectric infrared ray detection element that receives infrared rays through an optical filter that transmits only the infrared rays emitted from the light emitting unit is disclosed in Patent Literature 4 (claim 1). In this detector, the infrared ray sensor is irradiated with infrared rays for measurement of a specific wavelength band, and gas detection is conducted using the fact that an increase in the ambient $CO_2$ concentration leads to a decrease in the quantity of infrared rays received by the infrared ray detection element (see the 17th 21st rows of the fourth column).

CITATION LIST

Patent Literature

[PTL 1] Japanese Unexamined Patent Application Publication No. 2007-292461
[PTL 2] Japanese Unexamined Patent Application Publication No. H05-60604
[PTL 3] Japanese Unexamined Patent Application Publication No. H05-346346
[PTL 4] Japanese Patent No. 2949286

SUMMARY OF INVENTION

Technical Problem

The infrared ray sensors described in Patent Literatures 1 to 3 can be used as a temperature sensor that detects abnormal heating or firing of an object for detection. In the infrared ray sensors described in Patent Literatures 1 to 3, relative temperature distribution detection based on a difference between the compensation temperature of a surrounding area that is not affected by the temperature of an object for detection and the temperature of an object for detection is performed. It is difficult to perform anomaly detection of an object for detection at high sensitivity only by the temperature detection because it is strongly affected by the ambient temperature.

The detector described in Patent Literature 4 can be used for detection of a gas anomaly such as smoking of an object for detection. However, abnormal heating before occurrence of a change in gas such as smoking cannot be detected only by the gas detection.

Combined use of the infrared ray sensor for temperature detection described in Patent Literatures 1 to 3 and the detector described in Patent Literature 4 allows simultaneous detection of temperature and gas. However, in an application where they are incorporated into an electronic apparatus or the like to detect anomalies of electronic components, a large space is required for detection, which is not practical and inhibits cost reduction.

As described above, a small infrared ray sensor capable of simultaneous detection of both temperature and gas and an infrared ray detection device including the same have not been known.

The present invention has been accomplished in view of the above circumstances and an exemplary object of the present invention is thus to provide an infrared ray sensor that is capable of making a plurality of different types of detection such as temperature detection and gas detection in a simple structure and that is small in size and low in cost, and an infrared ray detection device including the same.

Solution to Problem

An infrared ray sensor according to an exemplary aspect of the invention includes, on one base, a first infrared ray detection unit that includes at least one infrared ray detection element including an infrared ray detection material with physical properties changing depending on properties of incident infrared rays, and receives and detects ambient infrared rays, and a second infrared ray detection unit that includes at least one infrared ray detection element having an identical element structure to the infrared ray detection element of the first infrared ray detection unit, is irradiated with infrared rays for measurement having specific physical properties, and detects a change in the physical properties of the infrared rays for measurement.

An infrared ray detection device according to an exemplary aspect of the invention includes an infrared ray sensor including, on one base, a first infrared ray detection unit that includes at least one infrared ray detection element including an infrared ray detection material with physical properties changing depending on properties of incident infrared rays and receives and detects ambient infrared rays, and a second infrared ray detection unit that includes at least one infrared ray detection element having an identical element structure to the infrared ray detection element of the first infrared ray detection unit, is irradiated with infrared rays for measurement having specific physical properties, and detects a change in the physical properties of the infrared rays for measurement, and an infrared ray irradiation means for selectively irradiating the second infrared ray detection unit of the infrared ray sensor with the infrared rays for measurement.

In this specification, "infrared ray" is defined as light within a wavelength band of about 750 to 1000 nm.

Advantageous Effects of Invention

According to an exemplary aspect of the present invention, it is possible to provide an infrared ray sensor that is capable of making a plurality of different types of detection such as temperature detection and gas detection in a simple structure and that is small in size and low in cost, and an infrared ray detection device including the same.

DESCRIPTION OF EMBODIMENTS

Figure 1:
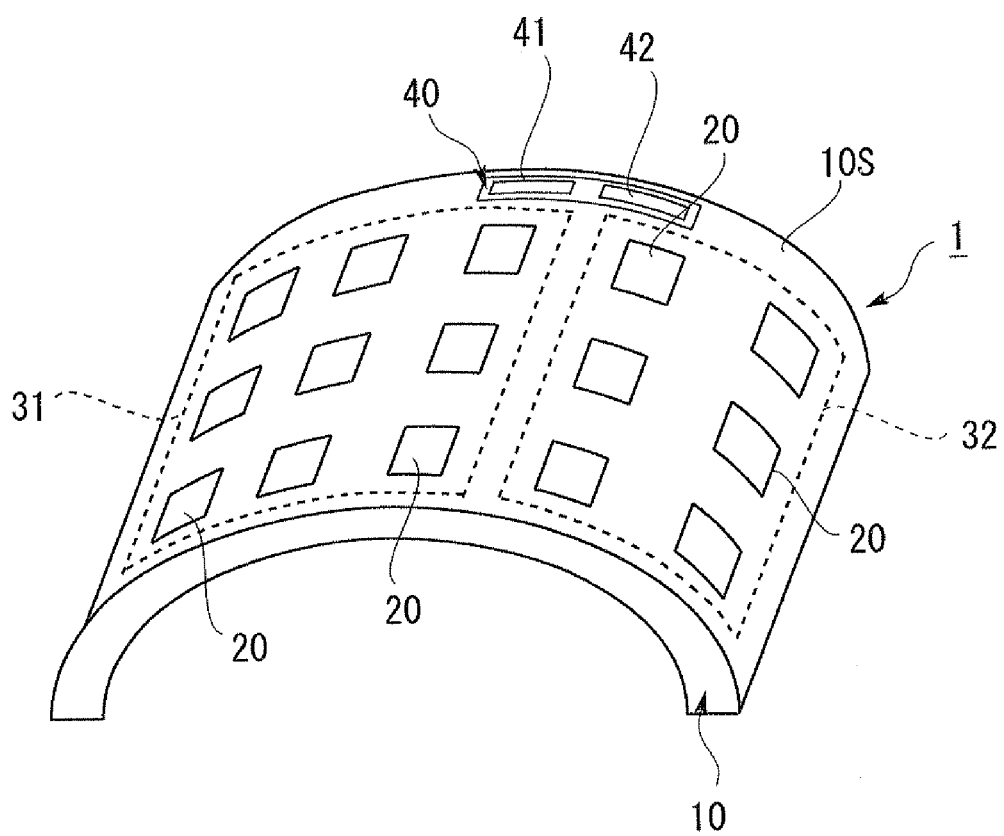
FIG. 1 is a fragmentary perspective view of an infrared ray sensor according to an exemplary embodiment of the present invention.
Figure 3:
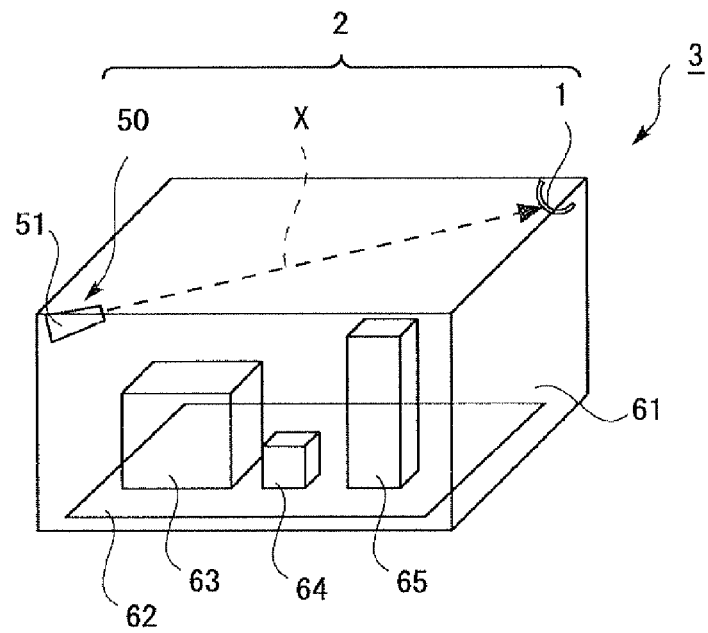
FIG. 3 is a perspective view of an infrared ray detection device according to an exemplary embodiment of the present invention and an electronic apparatus incorporating the same.
Figure 4:
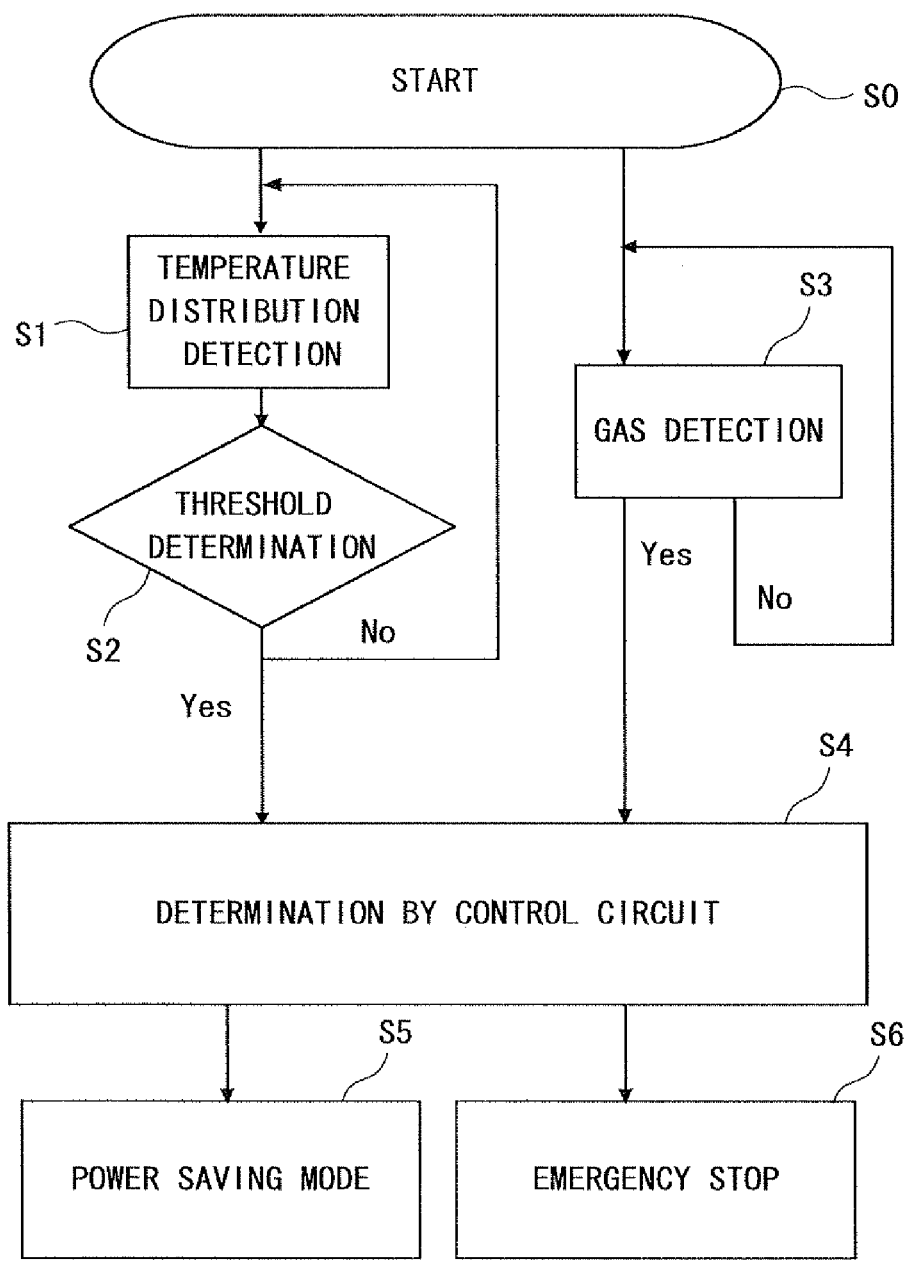
FIG. 4 is a flowchart showing a detection and control method using the infrared ray detection device in FIG. 3.

Structures of an infrared ray sensor according to an exemplary embodiment of the present invention and an infrared ray detection device including the same are described hereinafter with reference to the drawings. FIG. 1 is a perspective view of the infrared ray sensor, FIG. 2 is a sectional view of the infrared ray sensor, FIG. 3 is a fragmentary perspective view of the infrared ray detection device and an electronic apparatus incorporating the same, and FIG. 4 is a flowchart showing a detection and control method using the infrared ray detection device.

Figure 2:
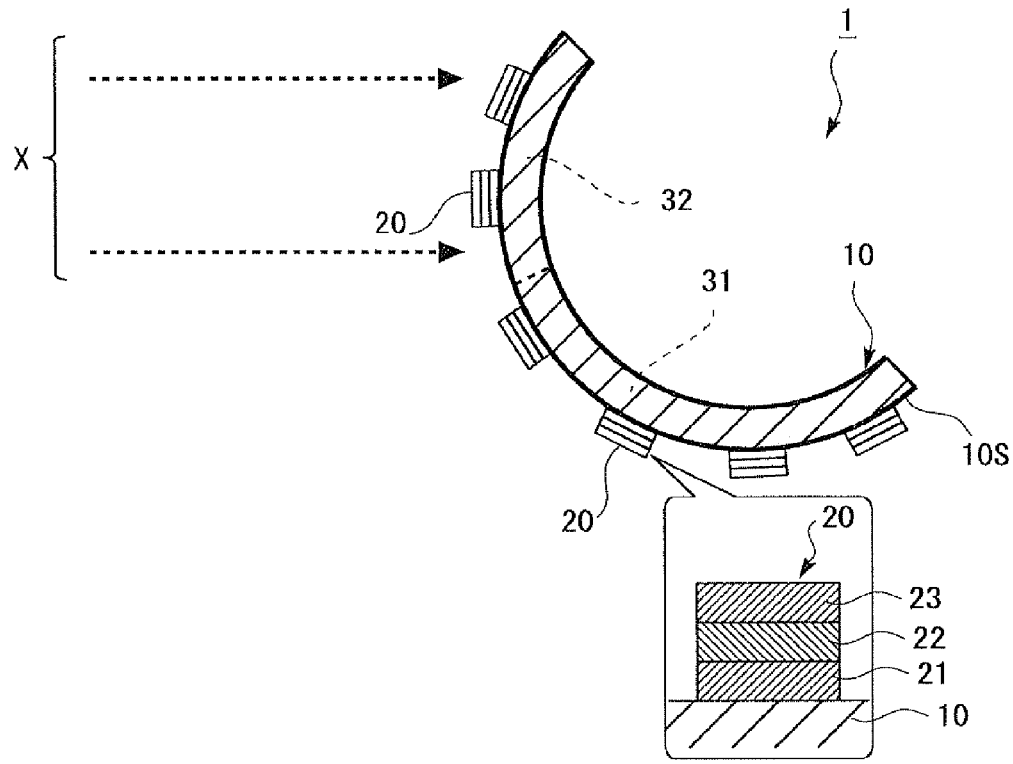
FIG. 2 is a sectional view of the infrared ray sensor in FIG. 1.

Referring to FIGS. 1 and 2, in an infrared ray sensor 1 according to this exemplary embodiment, on a convex surface 10S of a curved base 10, a plurality of pyroelectric elements (infrared ray detection elements) 20 are formed, each of which is made up of a stack of a first electrode (lower electrode) 21, a pyroelectric material (infrared ray detection material) 22 and a second electrode (upper electrode) 23 from the base side.

In this exemplary embodiment, the first electrode 21 and the second electrode 23 are patterned into the same rectangular shape when viewed from above. The first electrode 21 may be a simple unpatterned electrode. When the curved base 10 is made of a conductive material such as metal, the curved base 10 may serve also as the first electrode 21.

In this exemplary embodiment, the curved base 10 has a shape such that a rectangular flat plate when viewed from above is curved in an arc shape when viewed in cross section, and a plurality of rectangular pyroelectric elements 20 when viewed from above are arranged in an array on the curved base 10. Various lines are connected to the plurality of pyroelectric elements 20, though not shown.

Because the curved base 10 having the above shape is used as a base in the infrared ray sensor 1, it is possible to pick up and detect infrared rays over a wider range with a small number of parts, without using a condenser lens such as a Fresnel lens.

The shape of the curved base 10 is not limited to the above-described curved shape as long as it has a convex surface and can pick up and detect infrared rays over a wider range. Suitable base shapes other than the above include a hemispherical shape. When a detection target area is small and there is no need to pick up infrared rays over a wide range, a flat plate without a convex surface may be used as a base.

The shape and layout pattern of the pyroelectric elements 20 may be designed as appropriate. The shape of the pyroelectric elements 20 may be a circle (perfect circle or oval) or the like. The pattern of the pyroelectric elements 20 may be a linear array pattern in which a plurality of narrow rectangular patterns are arranged only in the width direction.

The material of the curved base 10 is not particularly limited, and examples of the material include:

various kinds of metal such as aluminum, copper, iron, titanium, and alloy of those metals;

various kinds of resin such as epoxy resin, acrylic resin, polyimide resin, and polycarbonate resin;

various kinds of ceramics such as alumina, silica and magnesia; and a compound of these elements, which are appropriately selected according to a desired shape, environment and the like.

The material of the electrodes 21 and 23 is not particularly limited, and examples of the material include nickel, platinum, palladium, gold black, and a combination of these elements. The material of the first electrode 21 and the material of the second electrode 23 may the same or not the same.

The electrodes 21 and 23 may be deposited using a known deposition method such as a liquid phase deposition method like the sol-gel process or a vapor phase deposition method like the MOCVD process.

When infrared rays are incident on the pyroelectric material 22, the surface charge caused by the pyroelectric effect is induced on the surface of the second electrode 23 according to the wavelength and quantity of the incident infrared rays. The induced surface charge is measured as an electrical signal to thereby detect the infrared rays.

The material of the pyroelectric material 22 is not particularly limited, and pyroelectric materials including ferroelectric ceramics such as lead zirconate titanate (PZT) ceramics and lithium tantalate ceramics, ferroelectric polymer such as polyvinylidene fluoride, and a compound of these elements are suitably used. Particularly, PZT ceramics with a high pyroelectric coefficient to maximally bring out the pyroelectric effect by the polarization process is preferred. "PZT" includes intrinsic PZT and its displacement.

The form of the first electrode 21, the pyroelectric material 22 and the second electrode 23 is not particularly limited, and they are preferably films because the film can be easily formed on the curved base 10 and allows the sensor 10 to be thinner and smaller.

When the first electrode 21, the pyroelectric material 22 and the second electrode 23 are in the form of films, the entire thickness of the pyroelectric elements 20 can be 1 to 100 µm or less, for example.

A method of depositing the pyroelectric material 22 is not particularly limited, and in the case of using the above-described ferroelectric ceramics, an aerosol deposition method that makes high-speed deposition of ceramic particles, a liquid phase deposition method like the sol-gel process, a vapor phase deposition method like the MOCVD process and the like may be employed.

A method of forming the pyroelectric material 22 may be a method that forms a ceramic film or ceramic plate on a sheet from slurry that contains a mixture of ceramic powder and binder by a method such as the tape-casting method, and attaches it onto the base 10.

For attachment of the ceramic film or ceramic plate onto the base 10, an adhesive material such as epoxy adhesive may be used. Although the thickness of the adhesive is not particularly limited, because an excessive thickness causes an increase in unnecessary electrical resistance component and leads to a decrease in infrared ray detection sensitivity, it is preferably 20 µm or less, for example.

If the material of the pyroelectric material 22 is the above-described ferroelectric polymer, it can be deposited by a known deposition method such as dissolving the polymer with solvent and then depositing and drying the polymer.

The patterning of a stack of the first electrode 21, the pyroelectric material 22 and the second electrode 23 may be performed by a known patterning technique such as photolithography.

The pyroelectric elements 20 may be formed on the curved base 10 that has been prepared in advance, or the pyroelectric elements 20 may be formed on a flat plate base and then they are curved together.

In the infrared ray sensor 1, the plurality of pyroelectric elements 20 are classified into two element groups, and one element group serves as a first infrared ray detection unit 31 that receives and detects ambient infrared rays, and the other element group serves as a second infrared ray detection unit 32 that is irradiated with infrared rays X for measurement having specific physical properties and detects a change in the physical properties of the infrared rays X for measurement.

In this exemplary embodiment, the first infrared ray detection unit 31 functions as a temperature detection unit that measures the temperature in the vicinity of the sensor, and the second infrared ray detection unit 32 functions as a gas detection unit that detects a change in components of the gas in the vicinity of the sensor.

On the curved base 10, a circuit unit 40 including a detection circuit (detection means) 41 that detects detection by the first infrared ray detection unit 31 and the second infrared ray detection unit 32 and a control circuit (control means) 42 that controls an object for detection based on the detection result of the detection circuit 41 is mounted in addition to the plurality of pyroelectric elements 20 described above. The control circuit (control means) 42 is connected to an object for detection such as an electronic component, and controls on/off, drive power and the like of the electronic component.

Referring to FIG. 3, an infrared ray detection device 2 according to this exemplary embodiment includes the infrared ray sensor 1 and an infrared ray irradiation means 50 that selectively irradiates the second infrared ray detection unit 32 of the infrared ray sensor 1 with the infrared rays X for measurement.

In this exemplary embodiment, the infrared ray irradiation means 50 is composed of an infrared light source 51 that emits the infrared rays X for measurement and a light guide optical system that guides the infrared rays X emitted from the infrared light source 51 according to need.

In this exemplary embodiment, the infrared light source 51 is placed opposite to the infrared ray sensor 1 and designed so that the infrared rays X are emitted with directivity from the infrared light source 51 toward the second infrared ray detection unit 32 of the infrared ray sensor 1. The infrared rays X for measurement may be output from the infrared light source 51 continuously or intermittently.

In order to prevent the first infrared ray detection unit 31 of the infrared ray sensor 1 from being irradiated with the infrared rays X for measurement, a desired light path of the infrared rays X from the infrared light source 51 to the second infrared ray detection unit 32 of the infrared ray sensor 1 may be surrounded by an infrared ray shielding member (not shown). Further, an infrared ray filter that selectively transmits the infrared rays X for measurement and does not transmit light with other wavelengths may be placed above the second infrared ray detection unit 32.

The first infrared ray detection unit 31 picks up infrared rays in the vicinity of the sensor and performs relative temperature distribution detection based on a difference between the temperature of an object for detection and the compensation temperature of the vicinity area that is not affected by the temperature of an object for detection. When a change occurs in the temperature distribution in the vicinity of the sensor due to abnormal heating or firing of an object for detection, the first infrared ray detection unit 31 can detect it.

The second infrared ray detection unit 32 is irradiated with the infrared rays X for measurement. The infrared rays X for measurement are absorbed or scattered by the gas existing in the light path from the light source 51 to the sensor 10, and the physical properties such as wavelength distribution and/or light quantity thereby change. The second infrared ray detection unit 32 detects a change in physical properties such as wavelength distribution and/or light quantity of the infrared rays X for measurement and thereby detects the gas existing in the light path. When a change occurs in gas composition in the vicinity of the sensor due to smoking of an object for detection, the second infrared ray detection unit 32 can detect it. The second infrared ray detection unit 32 can detect any type of gas generated in the vicinity.

Because the temperature detection by the first infrared ray detection unit 31 is strongly affected by the ambient temperature, it is difficult to perform anomaly detection of an object for detection at high sensitivity only by the temperature detection. Further, abnormal heating before occurrence of a change in gas such as smoking cannot be detected only by the gas detection by the second infrared ray detection unit 32. In this exemplary embodiment, both of them are included, so that abnormal heating, firing and smoking of an object for detection can be detected at high sensitivity.

In the infrared ray sensor 1 according to this exemplary embodiment, the first infrared ray detection unit 31 that receives and detects ambient infrared rays, and the second infrared ray detection unit 32 that is irradiated with the infrared rays X for measurement having specific physical properties and detects a change in the physical properties of the infrared rays X for measurement are mounted on the same base 10, thus enabling a plurality of different types of detection such as temperature detection and gas detection with one small sensor 1.

In the infrared ray sensor 1 according to this exemplary embodiment, because the curved base 10 is used as a base, a condenser lens such as a Fresnel lens is not needed, an infrared filter is not essential, the structure is simple, and sealing of the sensor 1 or the like is not necessary.

The infrared ray detection device 2 according to this exemplary embodiment can be used as a device that is mounted on various types of electronic apparatus and detects anomalies of electronic components.

FIG. 3 schematically shows an example in which the infrared ray detection device 2 according to this exemplary embodiment is incorporated into an electronic apparatus 3. In the electronic apparatus 3, a plurality of electronic components 63 to 65 formed on a substrate 62 are contained within a housing 61. In this example, the electronic components 63 to 65 are placed on the bottom side of the housing 61, and the infrared ray detection device 2 is placed on the top side of the housing 61. The infrared ray sensor 1 and the infrared light source 51 that constitute the infrared ray detection device 2 are arranged at diagonal positions on the top side of the housing 61. The present invention, however, is not limited thereto, and the layout of the infrared ray sensor 1 and the infrared light source 51 is designed as appropriate.

In the infrared ray sensor 1, the detection circuit (detection means) 41 that detects detection by the first infrared ray detection unit 31 and the second infrared ray detection unit 32 and the control circuit (control means) 42 that controls an object for detection based on the detection result of the detection circuit 41 are mounted on the curved base 10, on which the first infrared ray detection unit 31 and the second infrared ray detection unit 32 are also mounted, as described earlier. In this exemplary embodiment, the control circuit 42 is electrically connected to the electronic components 63 to 65 and controls on/off, drive power and the like of those components.

An example of detection and control method using the infrared ray detection device 2 is described hereinafter with reference to FIG. 4.

In the first infrared ray detection unit 31, the surface charge caused by the pyroelectric effect is induced on the surface of the second electrode 23 according to the wavelength and quantity of the incident infrared rays, and the surface charge is input as an electrical signal to the detection circuit 41, then temperature detection is done (Step S1), and threshold determination is made (Step S2). In Step S2, when the temperature is determined to be higher than a threshold, the information is input to the control circuit 42. In the infrared ray sensor 1, the temperature distribution of the space in the vicinity of the sensor can be detected because a plurality of pyroelectric elements 20 are arranged in an array.

In the second infrared ray detection unit 32, the surface charge caused by the pyroelectric effect is induced on the surface of the second electrode 23 according to the wavelength and quantity of the incident infrared rays X for measurement, and the surface charge is input as an electrical signal to the detection circuit 41, and then gas detection is done (Step S3).

The detection result by the detection circuit 41 is input to the control circuit 42. The control circuit 42 makes determination as to whether it is normal level or abnormal level based on both of data of the temperature detection result and data of the gas detection result, and controls on/off, drive power and the like of the electronic components 63 to 65 based on the determination result (Step S4).

For example, when the temperature is determined to be higher than a threshold in Step S2 and/or the existence of abnormal gas is detected in Step S3, the control circuit 42 controls the electronic components 63 to 65 to enter power saving mode (Step S5) or make emergency stop (Step S6). When heating of an object for detection is detected and its level is not very serious, the electronic apparatus 3 is controlled to enter power saving mode. On the other hand, in the emergency conditions where firing or smoking is detected, the electronic apparatus 3 is controlled to make emergency stop immediately.

As described above, according to this exemplary embodiment, it is possible to provide the infrared ray sensor 1 that is capable of making a plurality of different types of detection such as temperature detection and gas detection in a simple structure and that is small in size and low in cost, and the infrared ray detection device 2 including the same.

(Design Change)

The present invention is not limited to the above-described embodiment, and various design changes may be made as appropriate without departing from the scope of the invention.

Although the infrared ray sensor 1 that includes the pyroelectric elements 20 as infrared ray detection elements is described above, the infrared ray detection elements may have any structure as long as it includes an infrared ray detection material whose physical properties change depending on the properties of incident infrared rays. Infrared ray detection elements other than the pyroelectric element include a variable resistance infrared ray detection element using the rate of change with temperature of the resistance of a material, a junction type infrared ray detection element using a change in electrical properties of a semiconductor p-n junction and the like.

In this exemplary embodiment, the aspect in which the detection circuit (detection means) 41 and the control circuit (control means) 42 are mounted on the curved base 10 on which the first infrared ray detection unit 31 and the second infrared ray detection unit 32 are mounted is described. In the infrared ray detection device 2, the detection circuit and the control circuit may be placed outside the sensor 1, not incorporated in the sensor 1.

Examples according to the present invention are described hereinbelow.

Example 1

Fabrication of Infrared Ray Sensor and Infrared Ray Detection Device

A 42 alloy metal sheet (with a thickness of 100 μm (0.1 mm)) having a rectangular shape of 45 mm by 30 mm was prepared as a base. In this example, the base serves also as a lower electrode.

On the base, a PZT ceramic film with a thickness of 15 μm was deposited by the aerosol deposition method. On the ceramic film, an upper electrode made of a silver-palladium alloy (with a mass ratio of 70/30) was deposited with a thickness of 5 μm. After that, the stack of the ceramic film and the upper electrode was processed into an array pattern in which a plurality of 5 mm by 5 mm squares are arranged in 3 rows by 5 columns, with an interval of 3 mm.

Some of the pyroelectric elements arranged in an array of 3 rows and 5 columns served as a first infrared ray detection unit that receives and detects ambient infrared rays, and the others served as a second infrared ray detection unit that is irradiated with infrared rays for measurement having specific physical properties and detects a change in the physical properties of the infrared rays for measurement.

A detection circuit that detects detection by the first infrared ray detection unit and the second infrared ray detection unit and a control circuit that controls an object for detection based on the detection result of the detection circuit were included in the sensor.

Finally, the entire sensor was curved in an arc shape, so that the base became a curved base. The curvature radius was 30 mm.

An infrared light source that emits infrared rays for measurement was placed opposite to the sensor, and thereby the infrared ray detection device according to this exemplary embodiment was obtained. As the infrared light source, an infrared lamp that emits infrared rays with a wavelength of about 750 to 1000 nm was used. In the infrared ray detection device, the sensor was fixed to maintain the curved shape of the base.

(Test)

As shown in FIG. 3, a general-purpose power supply unit (150×140×86 mm) and the above-described infrared ray detection device are incorporated within one housing, and thereby an electronic apparatus was obtained. As the general-purpose power supply unit, the following three types having the same specification were prepared, so that three types of electronic apparatus were obtained.

Model 1: Operating normally (normal item)

Model 2: Abnormal heating occurring during operation (heating item)

Model 3: Smoking occurring during operation (smoking item)

The above three types of electronic apparatus were driven in the same environment and under the same driving conditions.

Figure 5A:
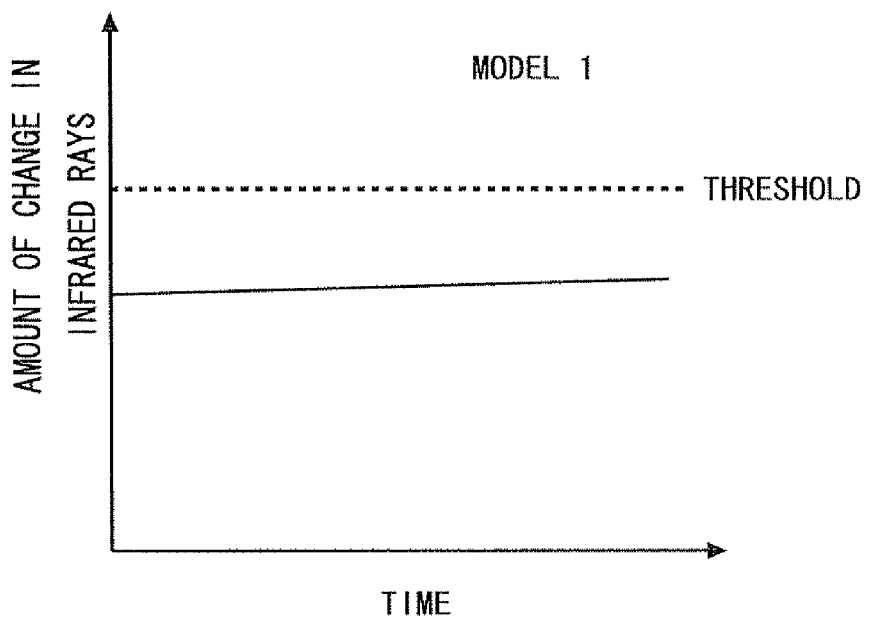
FIG. 5A is a graph showing a temperature detection result of a model 1 (normal) using the infrared ray detection device of an example 1.
Figure 5B:
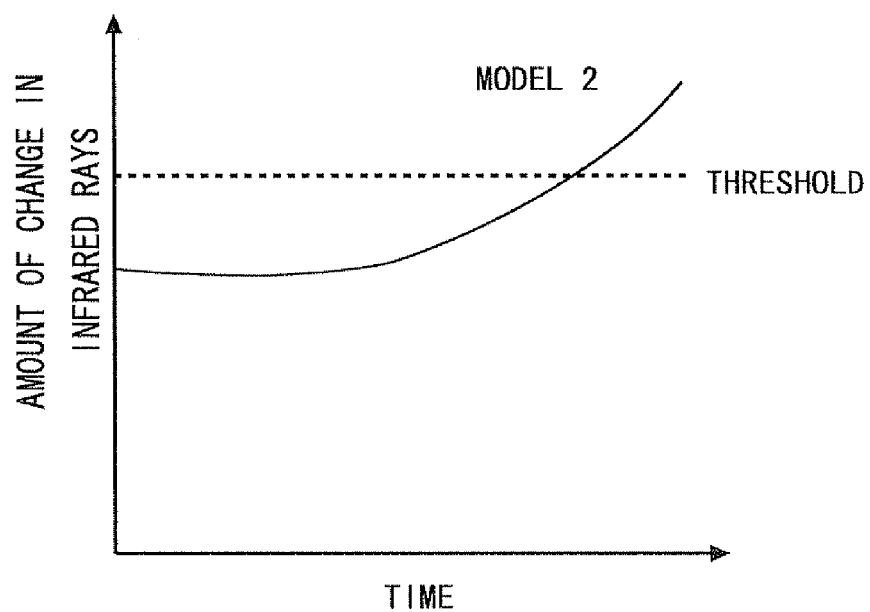
FIG. 5B is a graph showing a temperature detection result of a model 2 (heating) using the infrared ray detection device of the example 1.

FIG. 5A shows a temperature detection result of the model 1 (normal item), and FIG. 5B shows a temperature detection result of the model 2 (heating item). In FIGS. 5A and 5B, the vertical axis indicates the infrared ray quantity. There is a correlation between the quantity of infrared rays in the vicinity of the sensor and the temperature in the vicinity of the sensor, and their changes result in the same behavior.

Figure 6A:
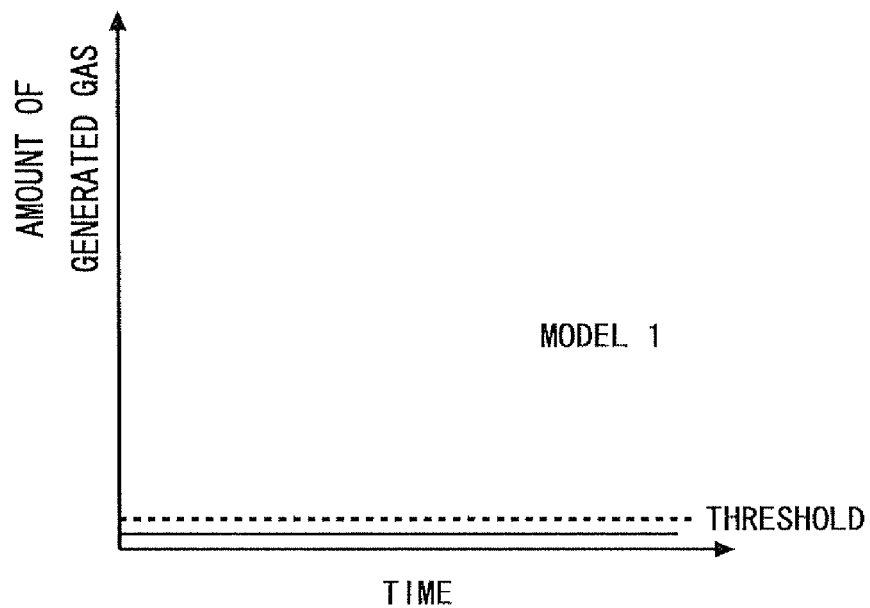
FIG. 6A is a graph showing a gas detection result of a model 1 (normal) using the infrared ray detection device of an example 1.
Figure 6B:
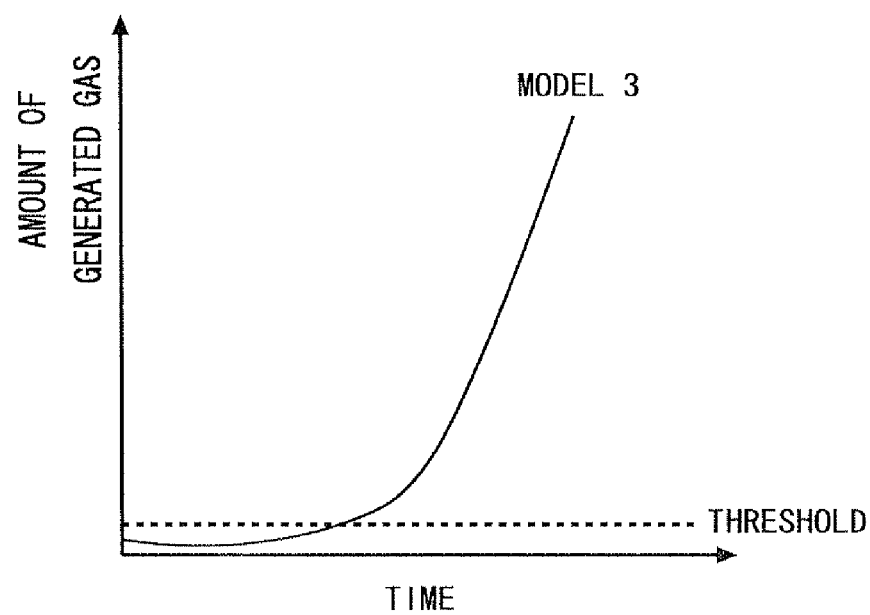
FIG. 6B is a graph showing a gas detection result of a model 3 (smoking) using the infrared ray detection device of the example 1.

FIG. 6A shows a gas detection result of the model 1 (normal item), and FIG. 6B shows a gas detection result of the model 3 (smoking item).

In this exemplary embodiment, the electronic apparatus was controlled to enter power saving mode at the point of time when the quantity of infrared rays exceeds a threshold, and the electronic apparatus was controlled to stop at the point of time when the amount of generated gas exceeds a threshold. Note that, because it is necessary to make emergency stop upon occurrence of gas generation, the threshold of gas detection was set lower than the threshold of temperature detection.

In the model 1, normal driving went on. In the model 2, a temperature increase due to abnormal heating was detected and it was switched to power saving mode. In the model 3, smoking was detected and driving was stopped. It was verified that, by incorporating the infrared ray detection device according to this exemplary embodiment into the electronic apparatus, abnormal heating and smoking were detected at high sensitivity and driving of the electronic apparatus was controlled suitably.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

This application is based upon and claims the benefit of priority from Japanese patent application No. 2010-031534 filed on Feb. 16, 2010 the disclosure of which is incorporated herein in its entirety by reference.

Reference Signs List

1 INFRARED RAY SENSOR
2 INFRARED RAY DETECTION DEVICE
3 ELECTRONIC APPARATUS
10 CURVED BASE
10 S CONVEX SURFACE
20 PYROELECTRIC ELEMENT (INFRARED RAY DETECTION ELEMENT)
21, 23 ELECTRODE
22 PYROELECTRIC MATERIAL (INFRARED RAY DETECTION MATERIAL)
31 FIRST INFRARED RAY DETECTION UNIT (TEMPERATURE DETECTION UNIT)
32 SECOND INFRARED RAY DETECTION UNIT (GAS DETECTION UNIT)
41 DETECTION CIRCUIT (DETECTION MEANS)
42 CONTROL CIRCUIT (CONTROL MEANS)
50 INFRARED RAY IRRADIATION MEANS
X INFRARED RAYS FOR MEASUREMENT

The invention claimed is:

1. An infrared ray sensor comprising, on one base:
a first infrared ray detection unit that includes at least one infrared ray detection element including an infrared ray detection material with physical properties changing depending on properties of incident infrared rays, and receives and detects ambient infrared rays; and
a second infrared ray detection unit that includes at least one infrared ray detection element having an identical element structure to the infrared ray detection element of the first infrared ray detection unit, is irradiated with infrared rays for measurement having specific physical properties, and detects a change in the physical properties of the infrared rays for measurement.

2. The infrared ray sensor according to claim 1, further comprising, on the base:
a detection unit for detecting detection by the first infrared ray detection unit and the second infrared ray detection unit.

3. The infrared ray sensor according to claim 2, further comprising, on the base:
a control unit for controlling an object for detection based on a detection result of the detection unit.

4. The infrared ray sensor according to claim 1, wherein
the first infrared ray detection unit is a temperature detection unit that measures ambient temperature, and
the second infrared ray detection unit is a gas detection unit that detects a change in components of ambient gas.

5. The infrared ray sensor according to claim 1, wherein the infrared ray detection element is a pyroelectric element including a pyroelectric material serving as the infrared ray detection material and a pair of electrodes sandwiching the pyroelectric material.

6. The infrared ray sensor according to claim 1, wherein the base has a convex surface, and the first infrared ray detection unit and the second infrared ray detection unit are formed on the convex surface.

7. An infrared ray detection device comprising:

an infrared ray sensor including, on one base, a first infrared ray detection unit that includes at least one infrared ray detection element including an infrared ray detection material with physical properties changing depending on properties of incident infrared rays and receives and detects ambient infrared rays, and a second infrared ray detection unit that includes at least one infrared ray detection element having an identical element structure to the infrared ray detection element of the first infrared ray detection unit, is irradiated with infrared rays for measurement having specific physical properties, and detects a change in the physical properties of the infrared rays for measurement; and an infrared ray irradiation unit for selectively irradiating the second infrared ray detection unit of the infrared ray sensor with the infrared rays for measurement.

8. The infrared ray detection device according to claim 7, further comprising:

a detection unit for detecting detection by the first infrared ray detection unit and the second infrared ray detection unit.

9. The infrared ray detection device according to claim 8, further comprising:

a control unit for controlling an object for detection based on a detection result of the detection unit.

10. An electronic apparatus comprising:

the infrared ray detection device according to claim 7; and an electronic component serving as the object for detection.

* * * * *